United States Patent
Cicchitti et al.

(10) Patent No.: US 11,946,862 B2
(45) Date of Patent: Apr. 2, 2024

(54) METHOD FOR IN-LINE ANALYSIS OF A COMPOSITE PRODUCT IN A MACHINE FOR THE PRODUCTION OF ABSORBENT SANITARY ARTICLES

(71) Applicant: Fameccanica.Data S.p.A., San Giovanni Teatino (IT)

(72) Inventors: Anselmo Cicchitti, San Giovanni Teatino (IT); Enrico Iavazzo, San Giovanni Teatino (IT)

(73) Assignee: Fameccanica.Data S.p.A.

( * ) Notice: Subject to any disclaimer, the term of this patent is extended or adjusted under 35 U.S.C. 154(b) by 270 days.

(21) Appl. No.: 17/381,411

(22) Filed: Jul. 21, 2021

(65) Prior Publication Data

US 2022/0023105 A1    Jan. 27, 2022

(30) Foreign Application Priority Data

Jul. 23, 2020  (IT) .......................... 102020000017836

(51) Int. Cl.
| | |
|---|---|
| *G01N 21/31* | (2006.01) |
| *G01N 21/25* | (2006.01) |
| *G01N 21/359* | (2014.01) |
| *G01N 21/59* | (2006.01) |
| *A61F 13/15* | (2006.01) |
| *A61F 13/53* | (2006.01) |
| *G01N 21/84* | (2006.01) |

(52) U.S. Cl.
CPC ........... *G01N 21/314* (2013.01); *G01N 21/25* (2013.01); *G01N 21/359* (2013.01); *G01N 21/59* (2013.01); *A61F 2013/1578* (2013.01); *A61F 2013/15821* (2013.01); *A61F 2013/530481* (2013.01); *G01N 2021/8444* (2013.01); *G01N 2021/845* (2013.01); *G01N 2021/8472* (2013.01)

(58) Field of Classification Search
CPC ........ A61F 13/15772; A61F 2013/1578; A61F 2013/15788; A61F 2013/15796; A61F 2013/15821; A61F 2013/530481; G01N 21/4738; G01N 21/94; G01N 2021/8444; G01N 2021/845; G01N 2021/8472; G01N 21/3563; G01N 21/359; G01N 21/314; G01N 21/25; G01N 21/55; G01N 21/59
See application file for complete search history.

(56) References Cited

U.S. PATENT DOCUMENTS

| | | | |
|---|---|---|---|
| 6,224,699 B1 * | 5/2001 | Bett ........................ | B65H 39/00 156/64 |
| 6,927,857 B2 | 8/2005 | Koele et al. | |
| 7,809,179 B2 * | 10/2010 | Singh .................... | G06T 7/0004 382/199 |
| 2015/0374557 A1 * | 12/2015 | Varga ..................... | H04N 23/90 382/103 |
| 2017/0128274 A1 * | 5/2017 | Varga ........................ | G01J 3/46 |
| 2018/0061038 A1 * | 3/2018 | Tan ............................ | G06T 7/11 |

FOREIGN PATENT DOCUMENTS

WO    2013090370 A1    6/2013

OTHER PUBLICATIONS

Italian Search Report dated Apr. 23, 2021. 7 pages.

* cited by examiner

*Primary Examiner* — Michael P LaPage
(74) *Attorney, Agent, or Firm* — RMCK Law Group PLC

(57) ABSTRACT

A method for in-line analysis of a composite product, wherein a hyperspectral sensor is used to acquire images of samples of target materials that are part of the composite product, in order to perform an in-line optical inspection at process speed.

5 Claims, 1 Drawing Sheet

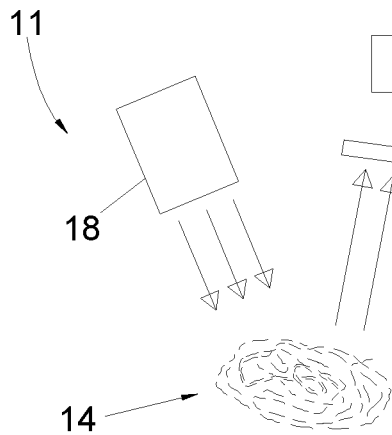
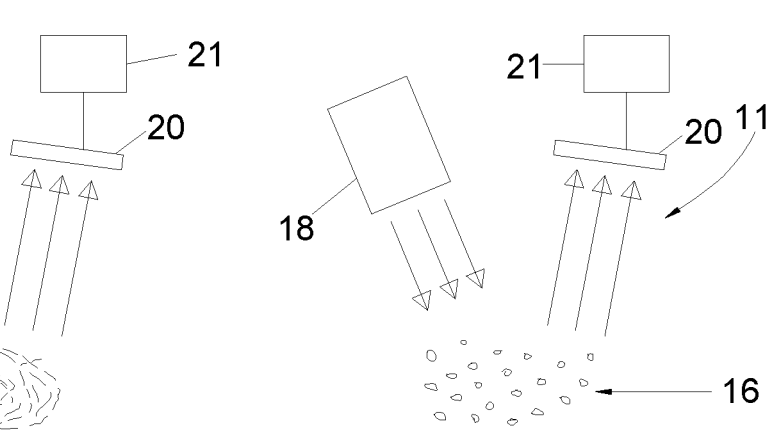
Fig.1a     Fig.1b
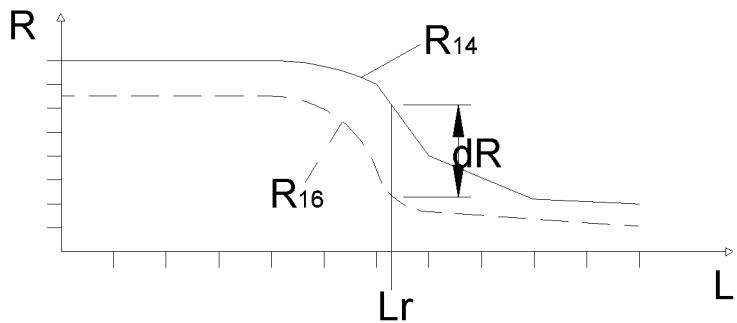
Fig.2
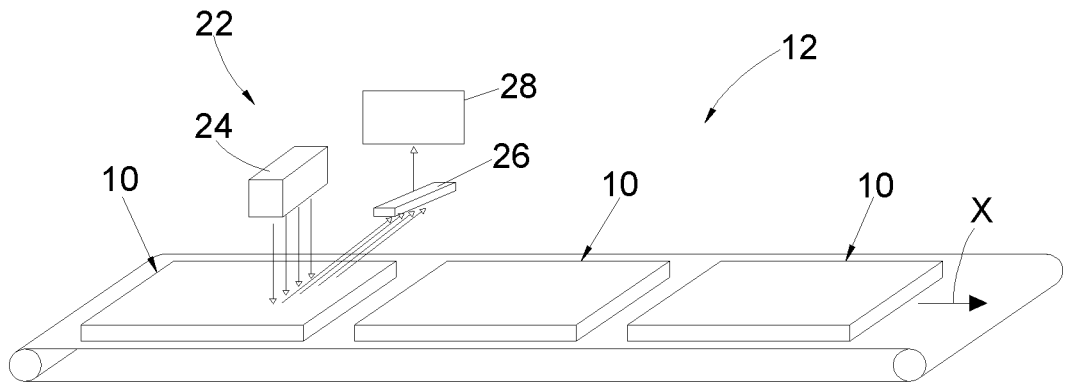
Fig.3
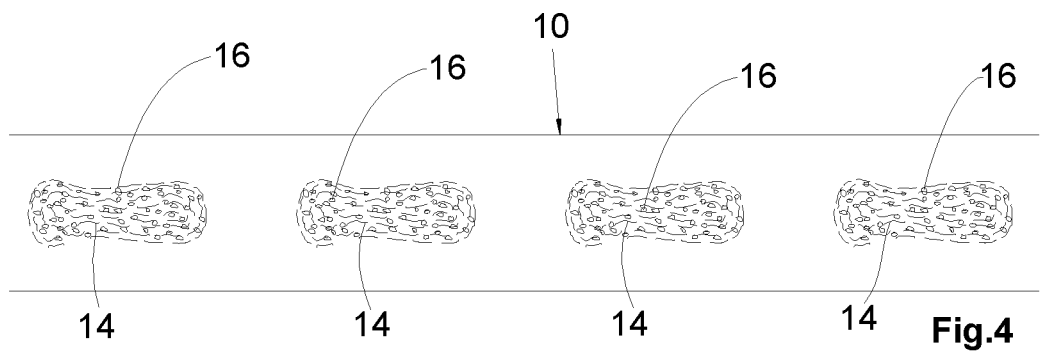
Fig.4

METHOD FOR IN-LINE ANALYSIS OF A COMPOSITE PRODUCT IN A MACHINE FOR THE PRODUCTION OF ABSORBENT SANITARY ARTICLES

CROSS-REFERENCE TO RELATED APPLICATION

This application claims priority to Italian Patent Application No. 102020000017836 filed Jul. 23, 2020. The disclosure of the above application is incorporated herein by reference in its entirety.

FIELD OF THE INVENTION

The present invention relates to the production of absorbent sanitary articles, and relates to a method for the in-line analysis of a composite product that advances in a machine for producing absorbent sanitary articles.

The analysis of composite products may have the object of determining parameters such as, for example, position, concentration, density, mass, or volume of one or more materials within the composite product. The product to be analyzed may be a continuous composite web or a discrete element, such as, for example, an absorbent core or a generic semi-finished product.

The invention was developed specifically to check, in-line, the position and concentration of a superabsorbent granular material (Super Absorbent Polymer or SAP) present in discrete absorbent cores, or in spaced apart areas of a continuous composite web.

DESCRIPTION OF THE PRIOR ART

In the sector of the production of absorbent sanitary articles there is a lot of interest in the in-line checking of some product characteristics, such as, for example, the composition of the absorbent cores, to determine the quality of the product and the correctness of the production processes.

For example, in processes involving the application of superabsorbent granular material on a fibrous sheet, with variable density in the longitudinal direction of the sheet, it is important to provide a control system to detect the density of the absorbent granular material applied onto the fibrous sheet. In fact, the discrete application of the absorbent granular material must be in phase with the fibrous sheet, to ensure that—in the finished product—the area containing the absorbent granular product is actually located in the area of the absorbent core that is struck by the flow of body fluids. Checking the density of absorbent granular material on the composite web allows correction, in-line, of the phase of the areas containing the absorbent granular material in cases wherein the dispensing device that delivers the superabsorbent granular material is not correctly in phase with the fibrous sheet.

Machines for producing absorbent sanitary articles containing discretely applied absorbent granular material are known, comprising a device for detecting the absorbent granular material. In a known solution, the detector device comprises a microwave resonator facing—at least in part— the continuous succession of absorbent cores advancing along a machine direction. The information provided by the detector device is used by a control unit in order to phase the dispensing device of absorbent granular material with a forming drum of the fibrous web if the deviation between the detected position of the absorbent granular material and the position of required application exceeds a defined threshold value.

Italian patent n. 102017000088859 by the same Applicant describes a method for detecting the density of absorbent granular material contained in a composite sheet, comprising: advancing a composite web in a longitudinal direction; emitting electromagnetic radiation with a frequency from 50 to 3000 GHz towards the composite web; receiving electromagnetic radiation transmitted through the composite web by means of a sensor sensitive to said electromagnetic radiation; and processing the signals provided by said sensor to obtain information on the density of the absorbent granular material contained in the composite web.

The main limitation of the known solutions described above consists in the fact that the physical principles on which they are based are unable to provide high resolution and repeatable measurements of the parameters to be controlled (for example, the position and concentration of SAP and the quantity of cellulose fluff and/or the distribution of both of these in the composite web) at the speeds with which the products on which to perform the measurements are made.

OBJECT AND SUMMARY OF THE INVENTION

The present invention aims to provide a method for in-line analysis of a composite product that overcomes the problems of the prior art.

According to the present invention, this object is achieved by a method having the characteristics forming the subject of claim 1.

The claims form an integral part of the disclosure provided here in relation to the invention.

The present invention envisages the use of a hyperspectral sensor to acquire images of isolated target materials that are part of the composite product to be analyzed, and to identify the reflectance of the isolated materials at various wavelengths. Subsequently, a determined wavelength is selected to display the materials of interest, and a narrowband optical sensor, for example, a Short-Wavelength Infrared (SWIR) sensor, is used to perform an in-line optical inspection at process speed on the selected wavelength.

The main advantage of the proposed solution is that it allows separation of the spectral responses of different materials that make up the composite product, and visual separation of the materials mixed within the product, with a high processing speed.

The solution according to the invention, therefore, allows optical detection—with a high resolution—of characteristics, parameters and production defects directly in-line and at the process speed.

BRIEF DESCRIPTION OF THE DRAWINGS

The characteristics and advantages of the present invention will become apparent from the detailed description that follows, given purely by way of non-limiting example, with reference to the attached drawings, wherein:

FIGS. 1a and 1b are schematic views illustrating a preliminary calibration station, FIG. 2 is a graph illustrating the spectral reflectance of two different materials, FIG. 3 is a schematic view of a vision apparatus that detects, in-line, images of a succession of composite products at a reference wavelength, and FIG. 4 is a schematic view illustrating an image of a composite web detected by a vision apparatus according to the present invention.

DETAILED DESCRIPTION

FIGS. 1-4 illustrate different steps of a method for the in-line optical analysis of a composite product indicated by 10 in FIG. 3.

The composite product 10 is formed in a machine for producing absorbent sanitary articles, indicated schematically by 12 in FIG. 3, by assembling together a plurality of different materials, such as cellulose fluff, superabsorbent granular material, non-woven sheets, elastic elements, etc. according to techniques known per se.

The composite product 10 may be a continuous composite web, or a discrete product (for example, an absorbent core), which is part of a continuous array of discrete products that are spaced apart along a feed direction X.

FIG. 1 illustrates, schematically, a preliminary calibration station 11 comprising a broad-spectrum illuminator 18, for example, a halogen illuminator, a hyperspectral sensor 20, and a first processing unit 21.

In the preliminary calibration station, a spectral analysis is carried out on two target materials 14, 16, of which certain parameters are to be analyzed, such as, for example, position, concentration, density, mass, or volume within the composite product 10. The two target materials 14, 16 are cellulose fluff and superabsorbent granular material. In the preliminary calibration step, two samples are formed, each of which consists of a single target material.

The spectral analysis consists of a measurement of the reflectance or reflection coefficient of the target materials 14, 16, as a function of the wavelength of the reflected radiation.

The samples of target materials 14, 16 are illuminated by the broad-spectrum illuminator 18, and the radiation reflected by the target materials 14, 16 is detected by the hyperspectral sensor 20. The hyperspectral sensor 20 provides signals to the processing unit 21, which are indicative of the reflectance value (or reflection coefficient) for very narrow and closely spaced wavelength ranges, covering a wide electromagnetic spectrum comprised, for example, from 952 to 1710 nm.

The processing unit 21 processes the signals received from the hyperspectral sensor 20, and determines the reflectances of the target materials 14, 16. The graph in FIG. 2 illustrates the reflectances R14, R16 of the target materials 14, 16 as a function of the wavelength L of the radiation.

The processing unit 21 is configured to identify a reference wavelength Lr at which the reflectance difference dR between the reflectances R14, R16 of the target materials 14, 16 is maximum.

The preliminary calibration step is only performed once before the operating step described below is initiated, and is repeated if the target materials change.

With reference to FIG. 3, the machine 12 comprises a vision apparatus 22 comprising an illuminator 24 arranged to illuminate the composite product 10 as it advances at the process speed in the direction X; an optical sensor 26 arranged to receive the radiation reflected by the composite product 10; and a second processing unit 28 that receives and processes the signals coming from the optical sensor 26.

The optical sensor 26 is a narrowband sensor that is only sensitive to electromagnetic radiation in a narrow range of wavelengths around the reference wavelength Lr, determined during the preliminary calibration step. The optical sensor 26 may have a measurement range of ±100 nm with respect to the reference wavelength Lr.

The illuminator 24 may also be a narrowband illuminator arranged to emit electromagnetic radiation only around the reference wavelength Lr.

In one embodiment, the illuminator 24 is configured to illuminate the composite product 10 with radiation having a wavelength range less than the measurement range of the optical sensor 26.

In a possible embodiment, the illuminator 24 may have an emission range of ±50 nm with respect to the reference wavelength Lr.

With target materials composed of cellulose fluff and superabsorbent granular polymers, the reference wavelength Lr, at which the reflectance difference between the target materials is maximum, is between 1300 nm and 1500 nm, which is in the short wavelength infrared range (SWIR). It is, therefore, possible to select an illuminator having an emission range of 1400 nm-1500 nm. Some embodiments envisage that the optical sensor 26 is a linear array of SWIR sensors combined with a band pass filter centered on the same reference wavelength.

Unlike broad spectrum hyperspectral analysis, optical analysis centered on a narrow wavelength range has very fast acquisition and processing times, which are consistent with the feed rates of the composite product in the process machine, which are between 100-800 meters/minute (m/min). On the market there are SWIR linear scan cameras with an acquisition frequency in the order of 30 KHz, which are able to acquire and process images of the composite product at the normal processing speeds of the products in machines for producing absorbent sanitary articles.

In the operating step, optical analysis of the composite product 10 centered on the reference wavelength Lr, at which the difference in reflectance between the target materials 14, 16 is maximum, allows optimization of the resolution of the images with respect to the target materials 14, 16.

At the output of the processing unit 28 it is, therefore, possible to obtain high resolution images that enhance the target materials 14, 16. FIG. 4 schematically shows an image of the composite product 10 processed by the processing unit 28, in which the two target materials 14, 16 are highlighted.

The processing of these images allows obtaining characteristic parameters of the target materials 14, 16 within the composite product 10, such as position, concentration, mass, volume, etc.

For example, it is possible to calculate the mass of the superabsorbent polymer (SAP) in a first way, which involves performing a calibration that associates a specific quantity of SAP with a signal detected by the optical sensor 26, or in a second way wherein, knowing the density of the SAP, and by measuring the volume percentage occupied by the SAP that is identified by the reflectance value, it is possible to estimate the mass of the SAP with high precision.

The solution according to the invention allows separation of the spectral responses of the target materials, which are part of the composite product. This enables visual highlighting of the mixed materials within the composite product, with a high resolution and processing speed. The solution according to the invention, therefore, allows optical detection of characteristics, parameters and production defects directly in-line, and at the process speed.

In particular, the use of a narrowband optical sensor focused on the wavelength at which the reflectance difference between the two target materials is maximum allows:

reduction of the energy,
performing the optical analysis at process speeds between 100 and 800 (m/min),
increasing the analysis resolution and the speed of image acquisition and processing.

When hyperspectral sensors become available with acquisition and processing speeds compatible with the process speeds of machines for producing absorbent sanitary articles, the vision apparatus 22 could employ a hyperspectral sensor instead of the narrowband optical sensor 26 to perform optical analysis on a wider spectrum of wavelengths.

In the above description, reference was made to the measurement of the reflected electromagnetic radiation (reflectance). In the case wherein the composite product is thin, the measurement on the electromagnetic radiation transmitted through the product (transmittance) may be carried out while maintaining all the other characteristics of the method.

Therefore, in the preliminary calibration step, the reflectance or spectral transmittance of each of the target materials is determined, and the reference wavelength is determined at which the difference between the reflectances or spectral transmittances of the target materials is maximum, and in the operating step, electromagnetic radiation is received, which is reflected from, or transmitted through, said composite product.

Of course, without prejudice to the principle of the invention, the details of construction and the embodiments can be widely varied with respect to those described and illustrated, without thereby departing from the scope of the invention as defined by the claims that follow.

The invention claimed is:

1. A method for in-line analysis of a composite product, the method comprising:
a preliminary step and an operating step,
wherein said preliminary step comprises:
arranging two samples of target materials, which are part of said composite product, composed of cellulose fluff and granular superabsorbent polymer (SAP), respectively,
carrying out a spectral analysis of said two samples of target materials using a first sensor,
determining spectral reflectance or transmittance data of each of said two samples of target materials, and
identifying a reference wavelength at which a difference between the spectral reflectances or transmittances of said two samples of target materials is maximum; wherein said reference wavelength is between 1300 nm and 1500 nm;
and wherein said operating step comprises:
advancing said composite product in a feed direction in a machine for producing absorbent sanitary products, at a speed from 100 to 800 m/min,
illuminating said composite product with electromagnetic radiation having an emission range including said reference wavelength,
receiving electromagnetic radiation reflected by, or transmitted through, said composite product by an optical sensor sensitive to said reference wavelength, and
processing signals provided by said optical sensor, and obtaining information on characteristic parameters of said two samples of target materials contained in the composite product.

2. The method of claim 1, wherein said optical sensor has a detection range that is greater than the emission range of the electromagnetic radiation that illuminates said composite product.

3. The method of claim 1, wherein the emission range of the electromagnetic radiation that illuminates said composite product is between ±50 nm around said reference wavelength.

4. The method of claim 1, wherein said optical sensor has a detection range of ±100 nm around said reference wavelength.

5. The method of claim 1, wherein said first sensor is a hyperspectral sensor.

* * * * *

UNITED STATES PATENT AND TRADEMARK OFFICE
CERTIFICATE OF CORRECTION

PATENT NO. : 11,946,862 B2  
APPLICATION NO. : 17/381411  
DATED : April 2, 2024  
INVENTOR(S) : Anselmo Cicchitti and Enrico Iavazzo Page 1 of 1

It is certified that error appears in the above-identified patent and that said Letters Patent is hereby corrected as shown below:

On the Title Page

Item (71) Applicant address information should be listed as:
- Fameccanica.Data S.p.A., San Giovanni Teatino (Chieti), ITALY -

Item (72) Inventor address information should be listed as:
- Anselmo Cicchitti, San Giovanni Teatino (Chieti), ITALY -
- Enrico Iavazzo, San Giovanni Teatino (Chieti), ITALY -

Signed and Sealed this  
Twenty-fifth Day of February, 2025

Coke Morgan Stewart  
*Acting Director of the United States Patent and Trademark Office*